US009730755B2

(12) United States Patent
Wittenberger et al.

(10) Patent No.: US 9,730,755 B2
(45) Date of Patent: Aug. 15, 2017

(54) MEDICAL DEVICE WITH ADJUSTABLE FLEXIBILITY

(71) Applicant: Medtronic CryoCath LP, Toronto (CA)

(72) Inventors: Dan Wittenberger, L'Î le-Bizard (CA); George D. Mallin, Montreal (CA); Claudia Lueckge, L'Î le-Bizard (CA); Mihai-Alexandru Ionescu, Dollard des Ormeaux (CA); Daniel Harvey-Poncelet, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 471 days.

(21) Appl. No.: 14/170,063

(22) Filed: Jan. 31, 2014

(65) Prior Publication Data

US 2015/0216589 A1   Aug. 6, 2015

(51) Int. Cl.
*A61B 18/14*     (2006.01)
*A61M 25/01*    (2006.01)
(Continued)

(52) U.S. Cl.
CPC ..... *A61B 18/1492* (2013.01); *A61M 25/0138* (2013.01); *A61M 25/0147* (2013.01);
(Continued)

(58) Field of Classification Search
CPC ........ A61B 18/1492; A61B 2017/2908; A61B 1/0017; A61B 1/00094; A61B 1/00142;
(Continued)

(56) References Cited

U.S. PATENT DOCUMENTS 6,866,628 B2    3/2005   Goodman et al.
7,041,052 B2 *  5/2006   Saadat ................. A61B 1/0055
                                                    600/114
(Continued)

FOREIGN PATENT DOCUMENTS

EP       1129670 A1    9/2001
EP       1487318 B1    3/2008
WO    2012/094135 A2   7/2012

OTHER PUBLICATIONS

International Search Report and Written Opinion dated Apr. 2, 2015 for International Application Serial No. PCT/CA2014/000909, International Filing Date: Dec. 22, 2014, consisting of 13 pages.

*Primary Examiner* — Nathan R Price
*Assistant Examiner* — Melissa A Snyder
(74) *Attorney, Agent, or Firm* — Christopher & Weisberg, P.A.

(57) ABSTRACT

A system and method for the delivery of a medical device to a treatment location. The device may include an elongate body, the elongate body including a plurality of annular segments and a jacket disposed about the plurality of annular segments and defining an interior space, and a vacuum source in fluid communication with the interior space of the jacket. When a vacuum is applied to the interior space of the jacket, the jacket may constrict about the plurality of annular elements, thereby increasing the frictional forces between the plurality of segments and between the plurality of segments and an inner surface of the jacket.

18 Claims, 12 Drawing Sheets

(51) Int. Cl.
  *A61B 18/00*   (2006.01)
  *A61B 18/02*   (2006.01)

(52) U.S. Cl.
  CPC .............. *A61M 25/0155* (2013.01); *A61B 2018/00351* (2013.01); *A61B 2018/00363* (2013.01); *A61B 2018/00577* (2013.01); *A61B 2018/0212* (2013.01)

(58) Field of Classification Search
  CPC . A61B 1/00135; A61B 1/00149; A61B 1/008; A61M 25/0155; A61M 25/0138; A61M 1/0037; A61M 1/0031; A61M 1/0045; A61M 16/0463
  See application file for complete search history.

(56) References Cited

U.S. PATENT DOCUMENTS

| | | | |
|---|---|---|---|
| 7,311,664 B2 | 12/2007 | Goodman et al. | |
| 7,611,455 B2 | 11/2009 | Borst et al. | |
| 7,794,387 B2 | 9/2010 | Olson et al. | |
| 8,025,620 B2 | 9/2011 | Olson et al. | |
| 8,460,172 B2 | 6/2013 | Meyer et al. | |
| 2005/0277945 A1* | 12/2005 | Saadat | A61B 17/06166 606/108 |
| 2005/0288626 A1 | 12/2005 | Koerner et al. | |
| 2006/0009752 A1 | 1/2006 | Lehmann et al. | |
| 2008/0039691 A1* | 2/2008 | Smith | A61B 1/0055 600/146 |
| 2008/0171976 A1 | 7/2008 | Rios et al. | |
| 2010/0094210 A1 | 4/2010 | Kastenhofer | |
| 2011/0208292 A1 | 8/2011 | Von Oepen et al. | |
| 2012/0010605 A1 | 1/2012 | Lehmann et al. | |
| 2013/0096535 A1 | 4/2013 | Gregorich et al. | |
| 2013/0184549 A1 | 7/2013 | Avitall et al. | |
| 2013/0184598 A1 | 7/2013 | Bowe et al. | |
| 2013/0253467 A1 | 9/2013 | Gianotti et al. | |
| 2014/0188054 A1 | 7/2014 | Iijima et al. | |

* cited by examiner

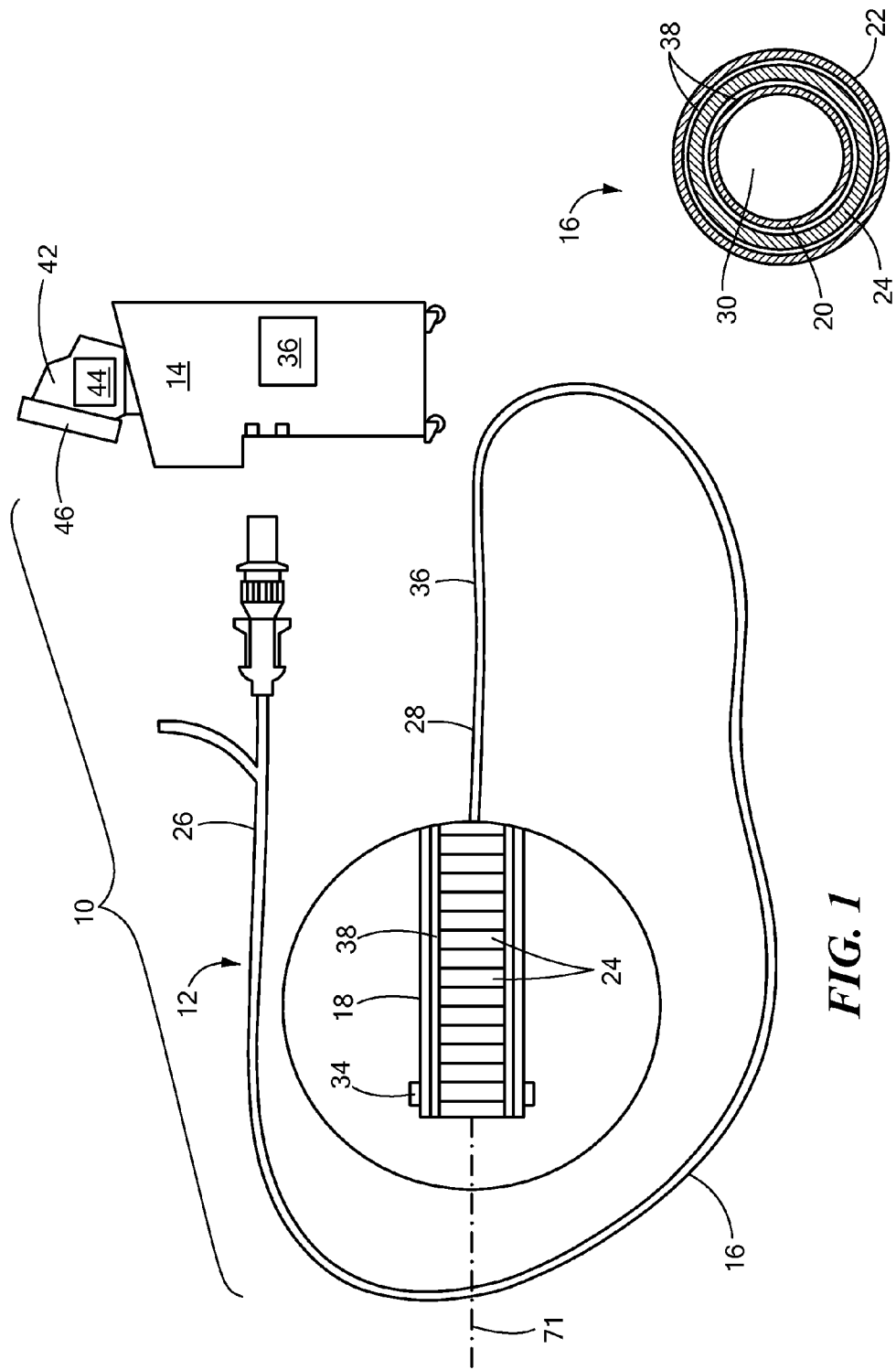

MEDICAL DEVICE WITH ADJUSTABLE FLEXIBILITY

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for delivering a medical device through a patient's vasculature to a target treatment site. The system may include an elongate body including a plurality of substantially annular segments and a jacket surrounding the plurality of segments. When a vacuum is applied to the jacket, the elongate body may be transitioned from a flexible state to a rigid state.

BACKGROUND OF THE INVENTION

Cardiac arrhythmia, or a disruption in the normal heartbeat rhythm, is a prevalent condition, causing more than 850,000 people to be hospitalized in the United States each year. There are several types of cardiac arrhythmia, including tachycardia (resulting in an abnormally fast heart rate), bradycardia/bradyarrhythmia (resulting in an abnormally slow heart rate), supraventricular arrhythmias (arrhythmias that originate in the atria), and ventricular arrhythmias (arrhythmias that originate in the ventricles).

There are several ways in which arrhythmias may be treated, one of which being catheter ablation, which may be an effective treatment for cardiac arrhythmia. However, there are difficulties associated with many of the commonly used procedures. For example, linear or spot ablation may be desired to treat a particular arrhythmogenic focus. In such a case, a focal catheter may be used. This catheter, or first a delivery sheath, is typically passed through the patient's vasculature into the heart to reach the target treatment site. In order to safely navigate through the tortuous vasculature pathways, the catheter and/or sheath must be highly flexible or steerable. However, in the case of focal catheters, the catheter must also be rigid enough to hold its shape without collapsing when pressed against the target tissue to make the ablation lesion.

Additionally, some aberrant electrical signals may originate from within one or more pulmonary veins, the ostia to which are located in the left atrium. Typical access to the left atrium includes a vascular pathway into the right atrium, through the septum, and into the left atrium. However, accessing the pulmonary veins once inside the left atrium may require difficult and precise steering of the catheter and/or sheath to reach the target treatment site. Some catheter designs include a portion of the elongate body including one or more bellows or accordion-like pleated areas, but these pleated areas do not lend rigidity to the catheter as well as flexibility, and the shape of the catheter must be maintained during treatment by internal rods, pull wires, or other means such as tensioning devices. Such means may significantly reduce the diameter of an inner lumen of the catheter, and are therefore unusable in over-the-wire catheters. Further, such configurations are unusable in guide sheaths, because the diameter of an inner lumen would not be sufficient to accommodate a treatment device therethrough.

Therefore, it is desired to provide a system and device that is easily navigated through the patient's vasculature into the heart but rigid enough to exert pressure against the target tissue, and that may be transitioned from a flexible state to a rigid or semi-rigid state without the need for internal rods, pull wires, tensioning devices, or other means.

SUMMARY OF THE INVENTION

The present invention advantageously provides a method and system for delivering a device into a patient's heart, wherein the device may be transitioned from a flexible state to a rigid or semi-rigid state. In one embodiment, a system for the delivery of a medical device may generally include an elongate body, the elongate body including a plurality of annular segments and a jacket disposed about the plurality of annular segments and defining an interior space, and a vacuum source in fluid communication with the interior space of the jacket. The plurality of segments may be coaxial or substantially coaxial with each other when the elongate body is in a linear configuration. Each of the plurality of segments may define a first opening and a second opening, and the elongate body may further include a central lumen, the central lumen being defined by at least the first opening of each of the plurality of segments. Further, the first opening of each of the plurality of segments may have a smaller diameter than the second opening, or an inner diameter of first opening may be substantially the same as an inner diameter of the second opening. Each segment may be, for example, annular. Alternatively, each segment may be concave and substantially hemispherical, and one or more of the plurality of segments may each be disposed within the concavity of an adjacent segment. Alternatively each segment may be hollow and conical, and one or more of the plurality of segments may each be disposed within the concavity of an adjacent segment. Alternatively, the plurality of segments may be formed form a continuous piece of material. When the vacuum source is activated, at least a portion of the jacket may be in contact with at least the first opening of each of the plurality of segments and/or at least a portion of an external surface of each of the plurality of segments. Activation of the vacuum source may cause the elongate body to transition from a flexible state to a rigid state. The plurality of segments may be movable with respect to each other when the elongate body is in the flexible state, and the plurality of segments may be immovable with respect to each other when the elongate body is in the rigid state.

In another embodiment, a system for the delivery of a medical device may include an elongate body, the elongate body including a plurality of annular segments, a jacket disposed about the plurality of annular segments and defining an interior space between the plurality of segments and an inner surface of the jacket, and a central lumen, the central lumen being defined by at least a portion of each of the plurality of annular segments, and a vacuum source in fluid communication with the interior space of the jacket, activation of the vacuum removing atmospheric air from the interior space of the jacket and increasing frictional forces between the plurality of annular segments and the inner surface of the jacket, the plurality of segments being movable with respect to each other when the vacuum source is inactive, and the plurality of segments are immovable with respect to each other when the vacuum source is activated. Optionally, the plurality of segments may be composed of a single piece of material.

A method for transitioning an elongate body between a flexible state and a rigid state may generally include providing an elongate body, the elongate body including: a plurality of annular segments, a jacket disposed about the plurality of annular segments and defining an interior space between the plurality of segments and an inner surface of the jacket, the interior space being in fluid communication with a vacuum source; and activating the vacuum source to remove at least a portion of atmospheric air from within the interior space.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 shows an exemplary system including an articulated focal catheter;

FIG. 2 shows a generalized anterior cross-sectional view of a segment of an elongate body of a guide sheath;

DETAILED DESCRIPTION OF THE INVENTION

Figure 3A:
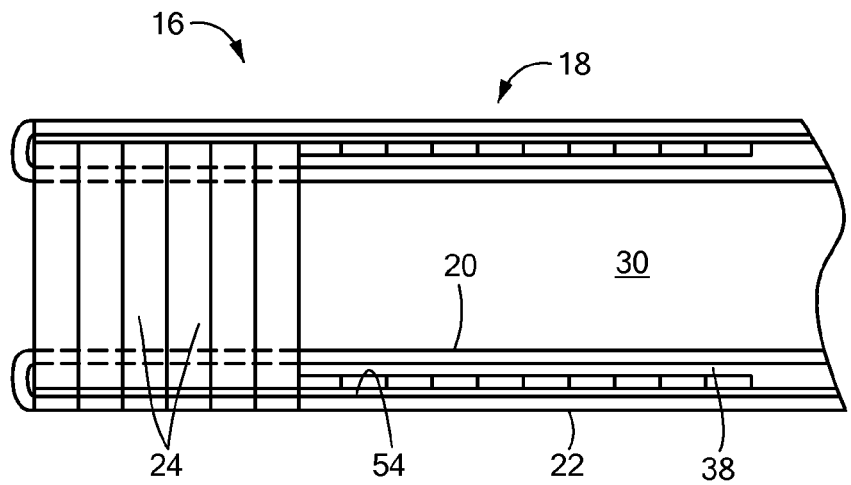
FIG. 3A shows a partial longitudinal cross-sectional view of a first embodiment of an elongate body of a guide sheath in a linear configuration.

The present invention provides a device and system that allows for the easy delivery of a medical device through a patient's vasculature to a target treatment site. In particular, the present invention provides an articulated medical device body that is flexible but may be rigid enough to be pressed against target tissue without collapsing. Referring now to the figures, which are not necessarily drawn to scale and are not intended to limit the scope of the invention, in which similar elements in different drawings are numbered with like reference numbers, an exemplary medical system 10 including an articulated focal catheter is shown. The system 10 shown in FIG. 1 may generally include a medical device 12 that may be coupled to a control unit 14 or operating console. The medical device 12, for example, a guide sheath as shown in FIG. 1, may generally include an elongate body 16 including a jacket 18 having an inner portion 20 and an outer portion 22, and a plurality of segments 24. The elongate body 16 may have a flexible state, in which each of the plurality of segments 24 are loosely associated with, adjacent to, or connected to adjacent segments 24. In this state, the elongate body 16 may be easily passed through tortuous patient vasculature. The elongate body 16 may also have a rigid state, in which a vacuum is applied to the inside of the jacket 18 (that is, between the inner portion 20 and the outer portion 22), thereby increasing frictional forces between the segments 24 and between the segments 24 and the inner surface of the jacket 18. This increase in frictional forces may "lock" the elongate body 16 in place, thus preserving any bends, twists, or other non-linear configurations the elongate body 16 may have at the time the vacuum is applied.

Continuing to refer to FIG. 1, the elongate body 16 may be passable through a patient's vasculature and/or proximate to a tissue region for diagnosis or treatment. Accordingly, the elongate body 16 and jacket 18 may be composed of a biocompatible material that is sufficiently flexible to safely pass through tortuous pathways of the patient's vasculature. For example, the jackets 18 may be composed of materials such as biocompatible polymers, PEBAX, nylon, or the like. To enhance flexibility, the elongate body 16 may include a plurality of segments 24. Various configurations of the segments 24 are shown in FIGS. 3A-6. The segments may be composed of materials such as PEBAX, nylon, Nitinol, or rigid or semi-rigid polymers.

The elongate body 16 may define a proximal portion 26 and a distal portion 28, and may further include one or more lumens or conduits disposed within the elongate body 16, such as a guidewire lumen 30 for procedures using an over-the-wire treatment and/or mapping device. Although not shown, the proximal portion 26 of the elongate body 16 may be in communication with a handle having one or more knobs, levers, connectors, umbilicals, and other components used for grasping and manipulating the device 12 and for connecting the device 12 to the control unit 14.

Optionally, the device 12 may further include one or more treatment and/or mapping elements 34 for energetic, therapeutic and/or investigatory interaction between the medical device 12 and a treatment site. For example, the treatment and/or mapping elements 34 may include one or more electrodes or other electrically and/or thermally conductive portions. The treatment and/or mapping elements 34 may deliver, for example, cryogenic therapy, radiofrequency energy, ultrasound energy, or may use other energy modalities to treat a tissue area in proximity to a target region, including cardiac tissue and/or pulmonary vein tissue. Additionally or alternatively, the one or more treatment and/or mapping elements 34 may be used to map electrical signals from target tissue, such as electrograms. Alternatively, the device 12 may not include treatment and/or mapping elements, and may instead be used solely as a guide sheath for a separate mapping and/or treatment device.

The treatment elements 34 may be located at a distal end of the device 12, and may, for example, be coupled to, affixed to, or integrated with the distal portion 28 of the elongate body 16. For example, the treatment elements 34 may be electrodes in electrical communication with the control unit 14 or thermally conductive areas that are cooled by a flow of refrigerant within. The treatment elements 34 may be of any suitable size, shape, or configuration. As a non-limiting example, the treatment elements 34 may be band-shaped electrodes or thermally conductive areas that substantially circumscribe the outer diameter of the elongate body 16. Additionally or alternatively, the device 12 may include one or more mapping elements (not shown) for recording electrical signals from cardiac tissue. Further, the device 12 may include one or more sensors, such as temperature, pressure, impedance, or pH sensors.

The system 10 may include one or more vacuums, treatment or diagnostic sources coupled to the device 12 for use in an operative procedure, such as tissue ablation. For example, the control unit 14 may include a vacuum pump 36 in communication with the space 38 within the jacket 18, between the inner jacket portion 20 and the outer jacket portion 22. Although a vacuum pump is discussed herein, it will be understood that other means for generating a vacuum may be used, such as a syringe used to withdraw air from within the jacket 18. This space 38 may be referred to as an interior space within the jacket 18, as shown and described in more detail in FIGS. 3A-6. The console 14 may include one or more fluid reservoirs to supply or recover fluid from one or more treatment devices, if used. Further, the control unit 14 may also include one or more energy sources 40, which may be in communication with the guide sheath device 12 (for example, in communication with one or more treatment and/or mapping elements 34) and/or one or independent more treatment and/or mapping devices, if used.

The control unit 14 may also include one or more components for the manual and/or automatic regulation of the system, such as a computer 42 having one or more processors 44 for executing one or more algorithms for the automatic operation of the device 12 before, during, and after a procedure. For example, the one or more processors 44 may be programmable to automatically initiate, modify, and/or stop a vacuum pump 36 from creating a negative-pressure environment within the space 38 within the jacket 18. Additionally, the one or more processors 44 may be programmable to automatically initiate, modify, and/or stop the flow of refrigerant into the distal portion of an independent treatment device and/or to receive and interpret physiological measurement signals from an independent mapping device, if used. The computer 42 may also include one or more displays 46 and/or user input devices for communicating system parameters, measurements from the device 12, alerts, warnings, or other operational values to the user and for accepting user controls.

Referring now to FIG. 2, a generalized cross-sectional view of an elongate body is shown. In FIG. 2, the segment 24 may be an annular segment, as shown in FIGS. 3A-3D. The inner surface (that is, the inner circumference) of the segments 24 may be covered by the inner jacket portion 20, and the outer surface (that is, the outer circumference) of the segments 24 may be covered by the outer jacket portion 22. When no vacuum is applied, there may be a gap or space 38 between the segment 24 and the jacket 18.

Referring now to FIGS. 3A-6, various embodiments of an elongate body of a guide sheath device are shown. In each embodiment, the elongate body 16 may include a jacket 18 having an inner portion 20 and an outer portion 22, and a plurality of segments 24. The inner and outer jacket portions 20, 22 may be joined together (for example, by using adhesives, heat bonding, chemical bonding, UV bonding, or the like) or the jacket 18 may be manufactured as a single piece of material. The overall shape of the jacket may be tubular (that is, cylindrical in shape with the central lumen 30 longitudinally disposed within). There may be a slight gap between the inner portion 20 and the outer portion 22, referred to as the interior space 38 within the jacket 18. The one or more segments 24 may be disposed within this interior space 38. For example, the segments 24 may be adjacent to each other. For example, a segment 24 may be immediately adjacent to or in direct contact with one or two other segments 24. Alternatively, the segments 24 may be at least partially nested within each other, and/or may be manufactured from a single piece of material. Further, it is contemplated that more than one of these segment configurations may be included in a single elongate body 16. The guidewire lumen 30 may be sized to accommodate not only a guidewire, but also a secondary medical device.

The jacket 18 may additionally include a distal portion and a proximal portion. The jacket distal portion may be closed (that is, not in communication with the external environment). The jacket proximal portion, on the other hand, may be open or at least partially open, and the opening may be in fluid communication with the negative pressure environment created by the vacuum pump 36. However, the open proximal portion may be closed to the external environment. As shown in FIGS. 4B and 5B, at least a portion of the jacket 18 may be in contact with an outer portion of each segment 24 and at least a portion of the jacket 18 may be in contact with an inner portion of each segment 24 when the vacuum is applied.

Figure 3B:
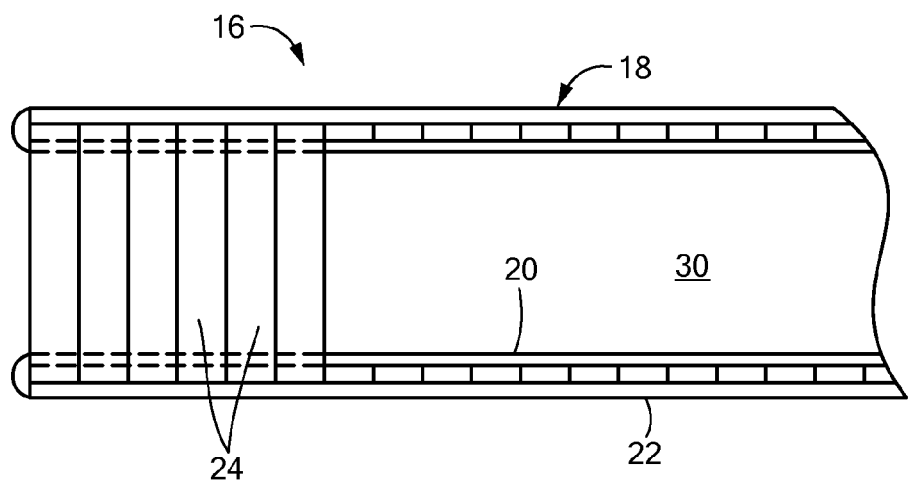
FIG. 3B shows a longitudinal cross-sectional view of the elongate body of FIGS. 3A and 3B, a vacuum being applied to the elongate body.
Figure 3C:
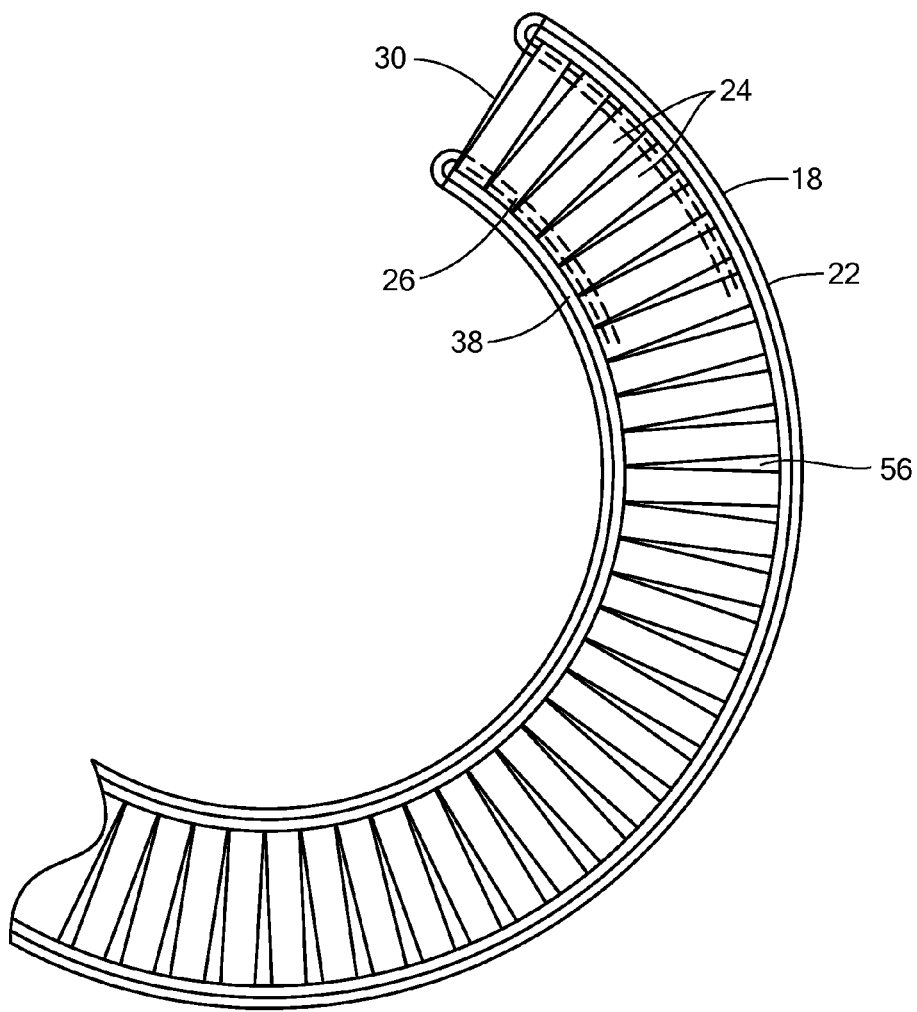
FIG. 3C shows a longitudinal cross-sectional view of the elongate body of FIG. 3A, the elongate body being in a curvilinear configuration.
Figure 3D:
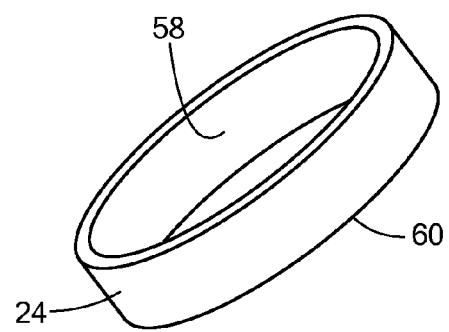
FIG. 3D shows a segment of the elongate body of FIGS. 3A-3C.

Referring particularly to FIGS. 3A-3D, a first embodiment of a guide sheath is shown. In this embodiment, each of the segments 24 may be annular rings. A side view of the segments 24 is shown in the first part of each of FIGS. 3A-3C, and a cross-sectional view of the segments 24 is shown in the second part of each of FIGS. 3A-3C. The central openings of the annular rings may define the guidewire lumen 30. Each segment 24 may include a first or distal opening 58 and a second or proximal opening 60. In the embodiment of FIGS. 3A-3D, the diameter of the first and second openings 58, 60 may be the same. For example, annular rings having a substantially flat outer surface and inner surface are shown (such as in FIG. 3D); however, it will be understood that the outer and/or inner surface may be rounded (convex), geodesic, textured, concave, or may have other configurations. FIG. 3A shows the elongate body 16 in a linear configuration with no vacuum applied, FIG. 3C shows the elongate body 16 in a curvilinear configuration with no vacuum applied. In this state, there may be a space or gap between the segments 24 and the inner surface 54 of the jacket 18. As shown in FIG. 3B, a vacuum applied to the elongate body 16 may cause the jacket 18 to constrict about the segments 24, thereby "locking" the elongate body into the present configuration. For example, when the vacuum is applied, at least a portion of the jacket 18 (such as the inner jacket portion 20) may be in contact with an external portion of each segment 24 and at least a portion of the jacket 18

(such as the outer jacket portion 22) may be in contact with an internal portion of each segment 24 (such as at least the circumference of the first opening 58 of each segment). It will be understood that the elongate body 16 may assume configurations other than those shown in the figures. Each segment 24 may be located next to adjacent segments 24, and may be in contact with adjacent segments 24. When the elongate body is in a flexible state, there may be some spaces or gaps 56 between adjacent segments 24, which may facilitate bending, twisting, and/or looping of the elongate body 16.

Figure 4A:
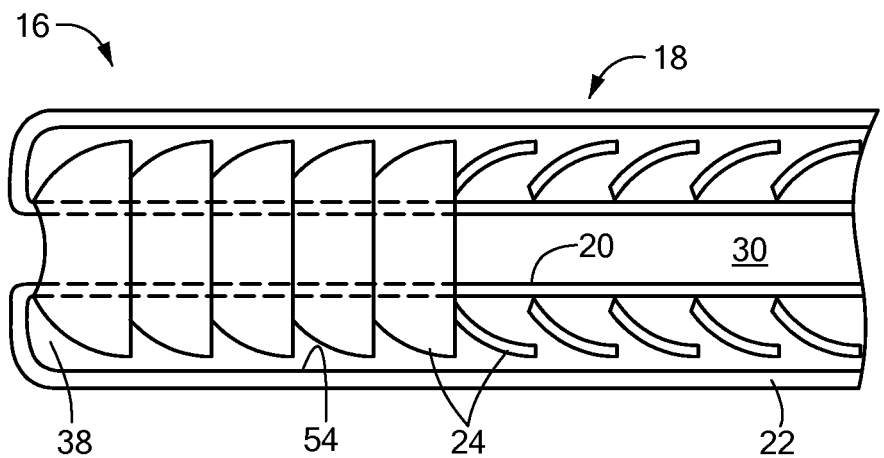
FIG. 4A shows a longitudinal cross-sectional view of a second embodiment of an elongate body of a guide sheath in a linear configuration.
Figure 4B:
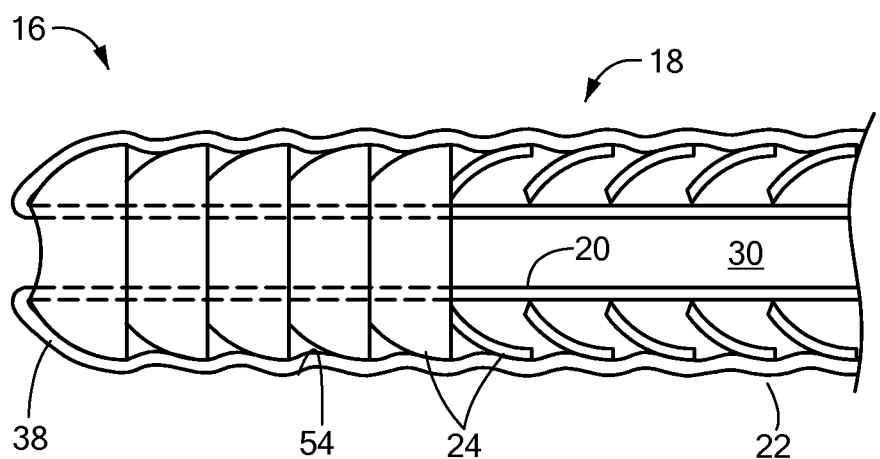
FIG. 4B shows a longitudinal cross-sectional view of the elongate body of FIGS. 4A and 4B, a vacuum being applied to the elongate body.
Figure 4C:
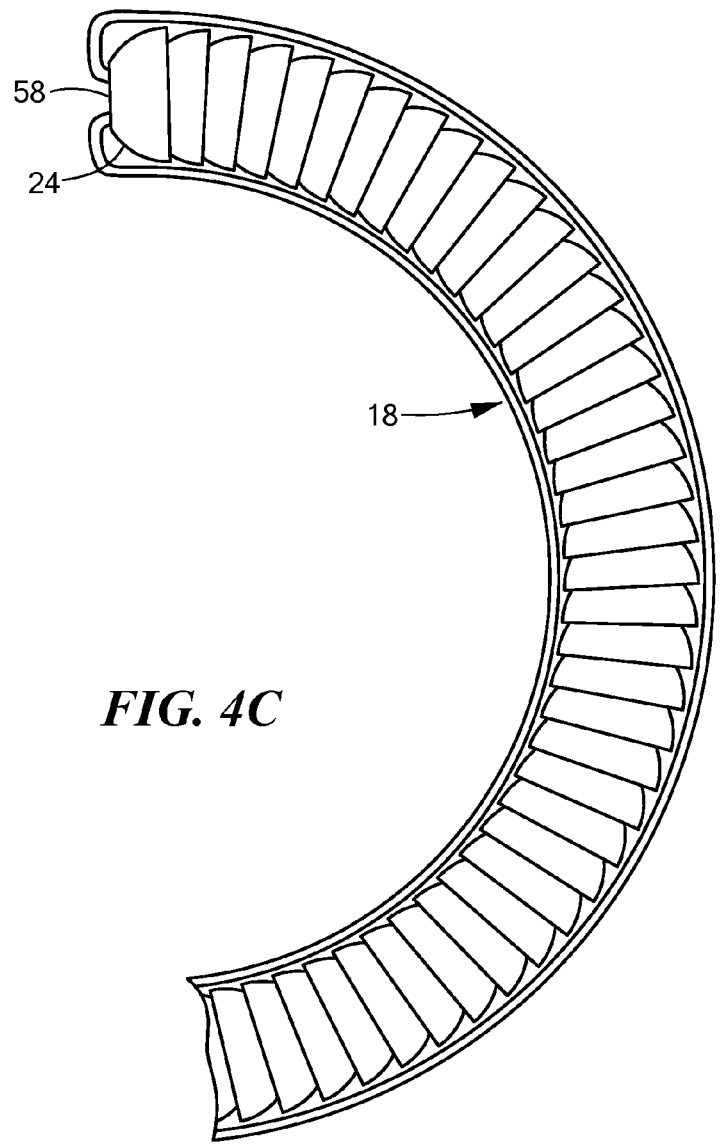
FIG. 4C shows a longitudinal cross-sectional view of the elongate body of FIG. 4A, the elongate body being in a curvilinear configuration.
Figure 4D:
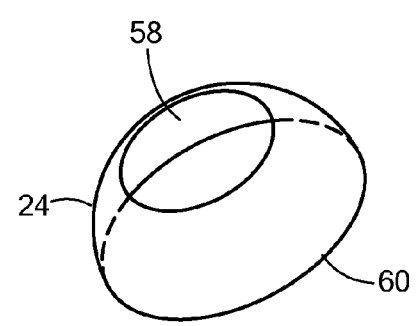
FIG. 4D shows a segment of the elongate body of FIGS. 4A and 4B.

Referring particularly to FIGS. 4A-4D, a second embodiment of a guide sheath is shown. In this embodiment, each of the segments 24 may be shaped like annular nesting hemispheres. For example, each segment 24 may have a concave or hollow annular shape, somewhat like a cup with a central opening (as shown in FIG. 4D). As shown, each segment 24 may be nested or at least partially located within the concavity of an adjacent segment 24. The first opening 58 of each segment may have a smaller diameter than the second opening 60 of each segment 24, and the first openings 58 of the plurality of segments 24 may define the maximum diameter of the guidewire lumen 30. Although the segments 24 are shown in FIGS. 4A-4C as having a smooth outer surface, it will be understood that the outer and/or inner surface may be smooth, textured, geodesic, or may have other configurations. Such non-smooth textures may enhance frictional forces between the segments 24 and between the segments 24 and the inner surface 54 of the jacket 18 when the vacuum 36 is applied. For example, when the vacuum is applied (as shown in FIG. 4B), at least a portion of the jacket 18 (such as the inner jacket portion 20) may be in contact with an external portion of each segment 24 and at least a portion of the jacket 18 (such as the outer jacket portion 22) may be in contact with an internal portion of each segment 24 (such as at least the circumference of the first opening 58 of each segment). Depending on the material and thickness of the jacket 18, the jacket 18 may at least partially conform to the shape of the segments 24, as shown in FIGS. 3B and 4B. FIG. 4A shows the elongate body 16 in a linear configuration without a vacuum 36 being applied, and FIG. 4B shows the elongate body 16 with a vacuum 36 being applied. FIG. 4C shows the elongate body 16 in a curvilinear configuration without a vacuum 36 being applied. When no vacuum 36 is applied to the jacket 18, there may be a space or gap between the segments 24 and the inner surface 54 of the jacket 18, as shown, for example, in FIG. 4A. It will be understood that the elongate body 16 may assume configurations other than those shown in the figures.

Figure 5A:
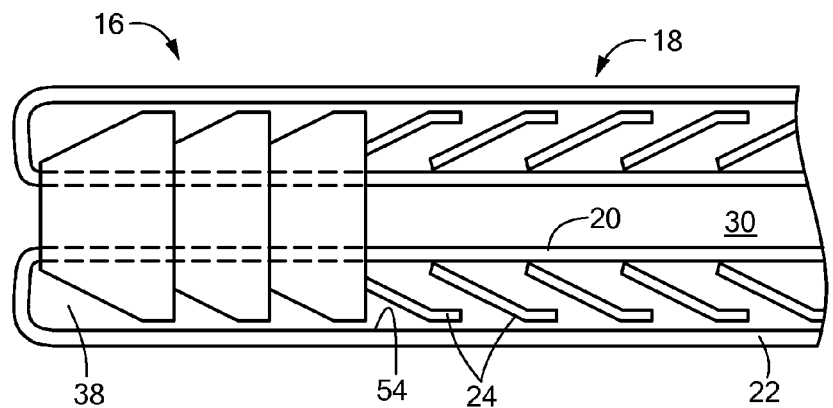
FIG. 5A shows a longitudinal cross-sectional view of a third embodiment of an elongate body of a guide sheath in a linear configuration.
Figure 5B:
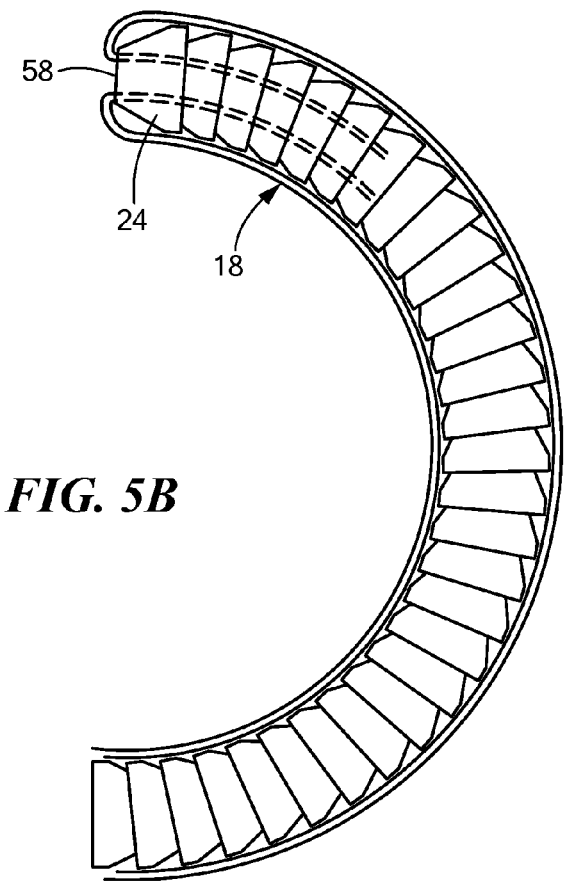
FIG. 5B shows a longitudinal cross-sectional view of the elongate body of FIG. 5A, the elongate body being in a curvilinear configuration.
Figure 5C:
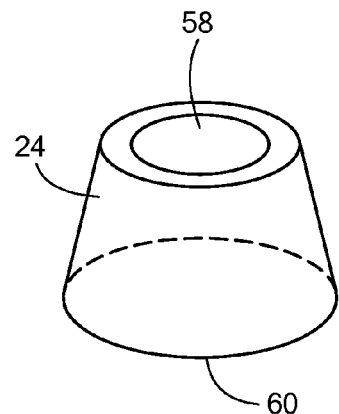
FIG. 5C shows a segment of the elongate body of FIGS. 5A and 5B.

Referring particularly to FIGS. 5A-5C, a third embodiment of a guide sheath is shown. In this embodiment, each of the segments 24 may be shaped like annular nesting cones. For example, each segment 24 may have an annular conical shape, somewhat like a hollow traffic cone with central opening (as shown in FIG. 5C). Each segment may include a flattened bottom portion proximate the second opening 60 (as shown in FIG. 5A) or may be continuously tapered from the first opening 58 to the second opening 60 (as shown in FIG. 5C). As shown, each segment 24 may be nested or at least partially located within the concavity of an adjacent segment 24. The first opening 58 of each segment may have a smaller diameter than the second opening 60 of each segment 24, and the first openings 58 of the plurality of segments 24 may define the maximum diameter of the guidewire lumen 30. Although the segments 24 are shown in FIGS. 5A and 5B as having a smooth outer surface, it will be understood that the outer and/or inner surface may be smooth, textured, geodesic, or may have other configurations. Such non-smooth textures may enhance frictional forces between the segments 24 and between the segments 24 and the inner surface 54 of the jacket 18 when the vacuum 36 is applied. Further, the length L of the segments may help define the flexibility of the elongate body 16. For example, segments having a greater length may cause the elongate body 16 to be less flexible than segments having a smaller length, because the minimum radius of curvature achievable by the elongate body 16 may be defined, at least in part, by the length L of each segment 24. In situations wherein more rigidity is desired and less flexibility is required, segments with a grater length L may be used. In contrast, segments with a smaller length L may be used in situations wherein more flexibility and a smaller minimum radius of curvature are required. FIG. 5A shows the elongate body 16 in a linear configuration without a vacuum 36 being applied, and FIG. 5B shows the elongate body 16 in a curvilinear configuration without a vacuum 36 being applied. When the vacuum is applied, at least a portion of the jacket 18 (such as the outer jacket portion 22) may be in contact with an external portion of each segment 24 and at least a portion of the jacket 18 (such as the inner jacket portion 20) may be in contact with an internal portion of each segment 24 (such as at least the circumference of the first opening 58 of each segment). As shown and described in FIG. 4B, depending on the material and thickness of the jacket 18, the jacket 18 may at least partially conform to the shape of the segments 24. When no vacuum 36 is applied to the jacket 18, there may be a space or gap between the segments 24 and the inner surface 54 of the jacket. It will be understood that the elongate body 16 may assume configurations other than those shown in the figures.

Figure 6:
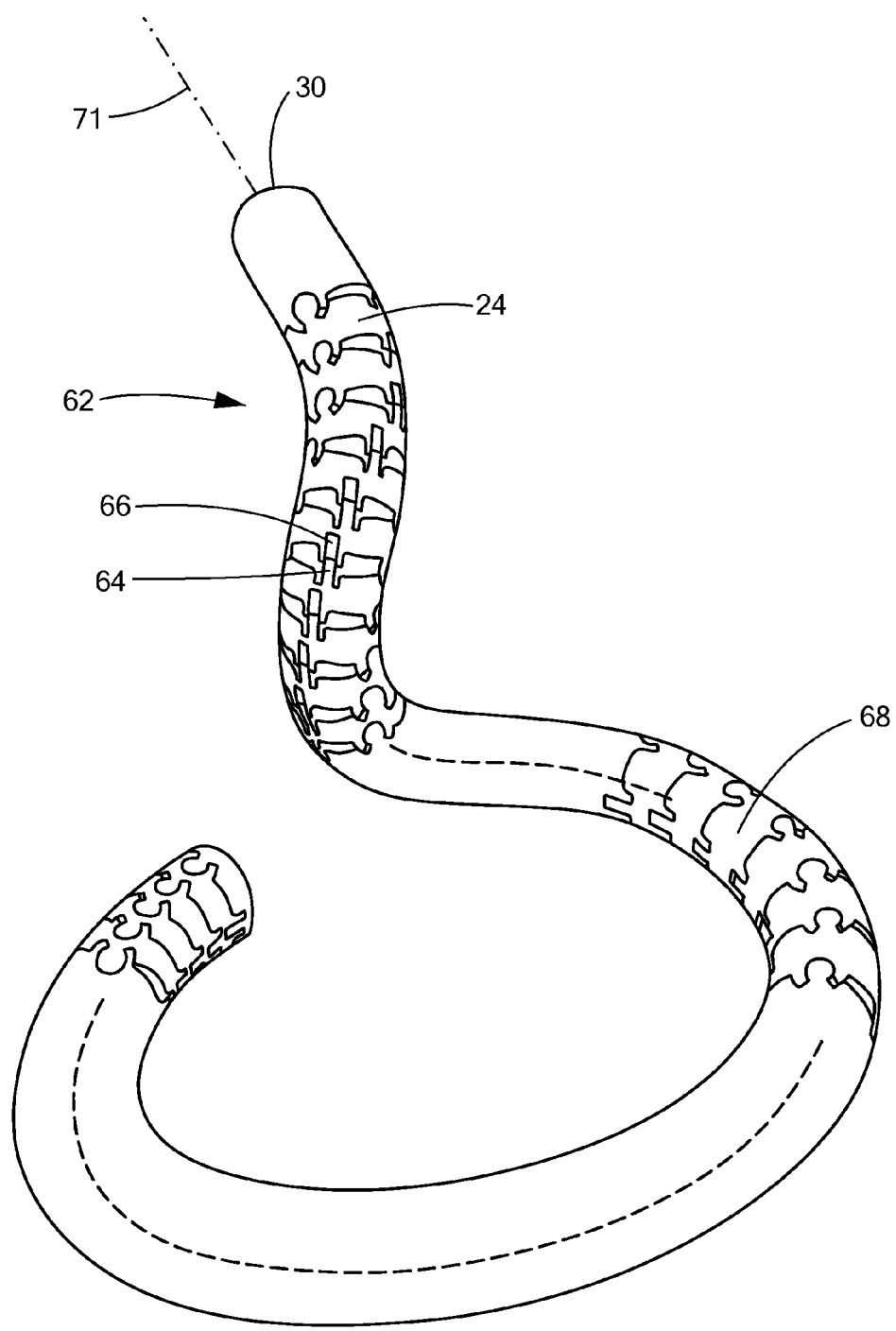
FIG. 6 shows a segment body that may be included in a fourth embodiment of an elongate body of a guide sheath, the segment body being in a curvilinear configuration.

Referring particularly to FIG. 6, a segment body that may be included in a fourth embodiment of a guide sheath is shown. In this embodiment, each of the annular segments 24 may be defined by a single piece of material (such as PEBAX, nylon, Nitinol, stainless steel, rigid or semi-rigid polymer, or the like). For example, a cylindrically shaped piece of material (such as a tube) may form the plurality of segments 24. The material may be machined, laser cut, molded, or may go through one or more other processes to produce the final product. This elongate piece of material that defines the segments 24 may be referred to as the segment body 62. The diameter of the segment body 62, and the diameter of the guidewire lumen within 30, may be constant or substantially constant along its length. The segments 24 may be manufactured such that each segment 24 has one or more protruding portions 64 and one or more indented portions 66, and the protruding portion 64 of one segment 24 may fit within the indented portion 66 of an adjacent segment 24. The segment body 62 may also include one or more openings or holes within the material. Further, there may be at least one continuous path 68 along the length of the segment body 62, even if the path or paths aren't linear. For example, the segment body 62 may include a tortuous continuous path 68 that serves to keep the segments 24 connected together. When in use, the elongate body 16 may be rotated if a desired bend would be inhibited by a continuous path 68. Although the segment body 62 is shown in FIG. 6 as having a smooth outer surface, it will be understood that the outer and/or inner surface may be smooth, textured, geodesic, or may have other configurations. Such non-smooth textures may enhance frictional forces between the segment body 62 and the inner surface 54 of the jacket 18 when the vacuum 36 is applied. For example, when the vacuum is applied, at least a portion of the jacket 18 (such as the outer jacket portion 22) may be in contact with an external portion of each segment 24 and at least a portion of the jacket 18 (such as the inner jacket portion 20) may be in contact with an internal portion of each segment 24 (such as at least the circumference of the first opening 58 of each segment). The segment body 62 is shown in FIG. 6 without the jacket 18 for clarity; however, it will be understood that a jacket 18 may cover the segment body 62 and define a guidewire lumen 30, as shown in FIGS. 1-5C. Further, the jacket 18 may be in communication with a vacuum source 36 to apply a vacuum to the elongate body 16 as shown and described above. It will be understood that the elongate body 16 may assume configurations other than that shown in FIG. 6.

Figure 7:
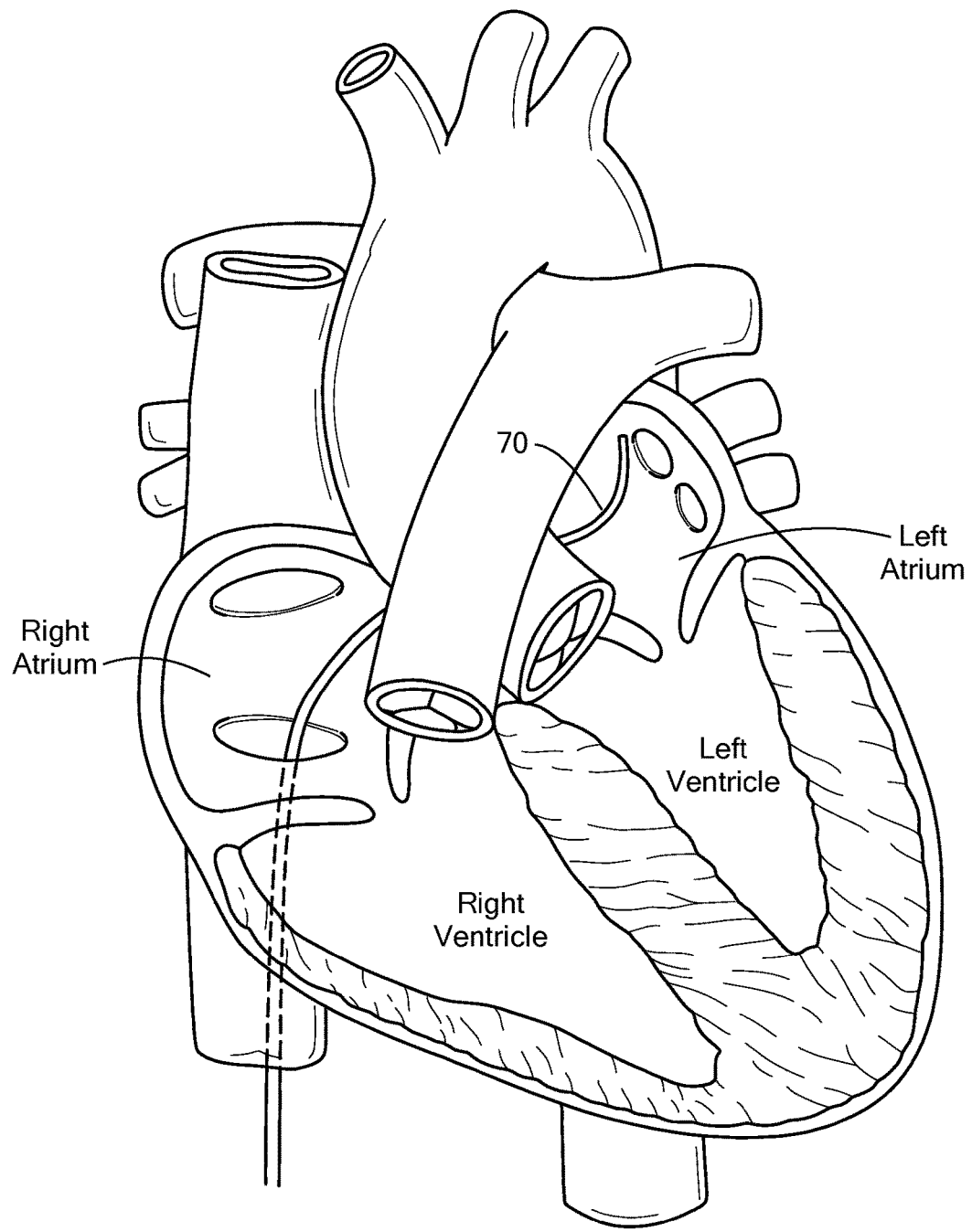
FIGS. 7-10 show a process for delivering a treatment and/or mapping device to a target area of a heart using a guide sheath described herein.
Figure 8:
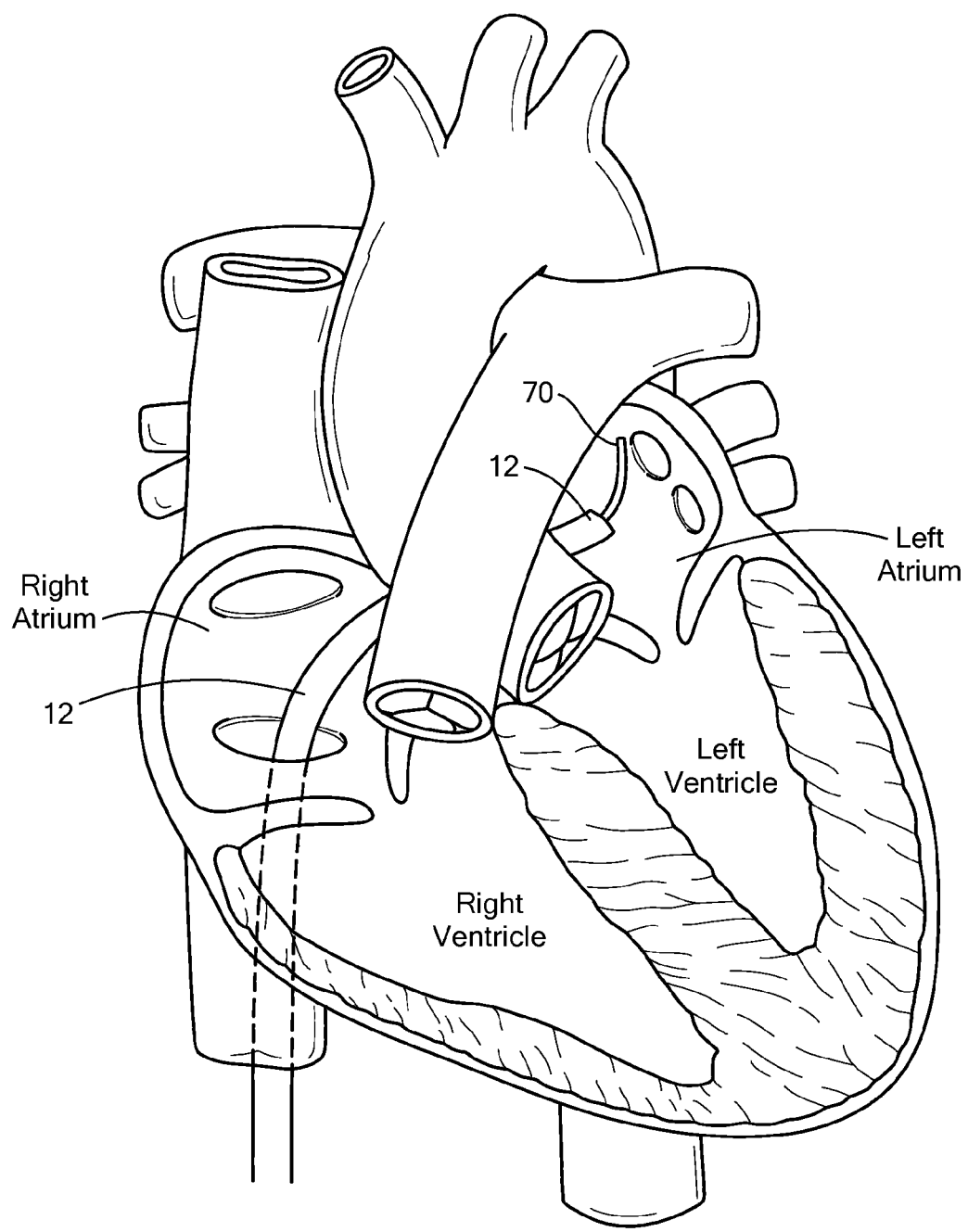

Referring now to FIGS. 7-10, a guidewire 70 may first be delivered to a location proximate a target treatment site (as shown in FIG. 7). The sheath 12 may then be advanced over the guidewire 70 until the distal portion 28 of the elongate body 16 is proximate a target treatment site (as shown in FIG. 8). The vacuum pump 36 may be switched off or may otherwise not be in communication with the interior space 38 within the jacket 18 while the elongate body 16 is being passed over the guidewire 70 through the patient's vasculature. In this configuration, the elongate body 16 may be very flexible, with the plurality of segments 24 moving easily in relation to each other. This may allow the elongate body 16 to follow the path of the flexible guidewire 70. The plurality of segments 24 may be coaxial or substantially coaxial with each other and radially disposed about the center line 71 of the guidewire lumen 30 when the elongate body 16 is in a linear or substantially linear configuration. When the elongate body 16 is bent during device placement, the one or more segments 24 may be off-axis relative to adjacent segments, but still radially disposed about the centerline 71 of the guidewire lumen 30. Additionally, the material from which the jacket 18 is composed may have a low enough durometer that allows for slight sideways or lateral movement of one or more segments 24 relative to adjacent segments. However, even when the segments 24 are substantially coaxial relative to each other, the plurality of segments 24 will be coaxial relative to the guidewire lumen 30 within the elongate body 16. That is, each segment 24 will encircle or partially encircle at least a portion of the guidewire lumen 30, as shown, for example, in FIG. 2.

Figure 9:
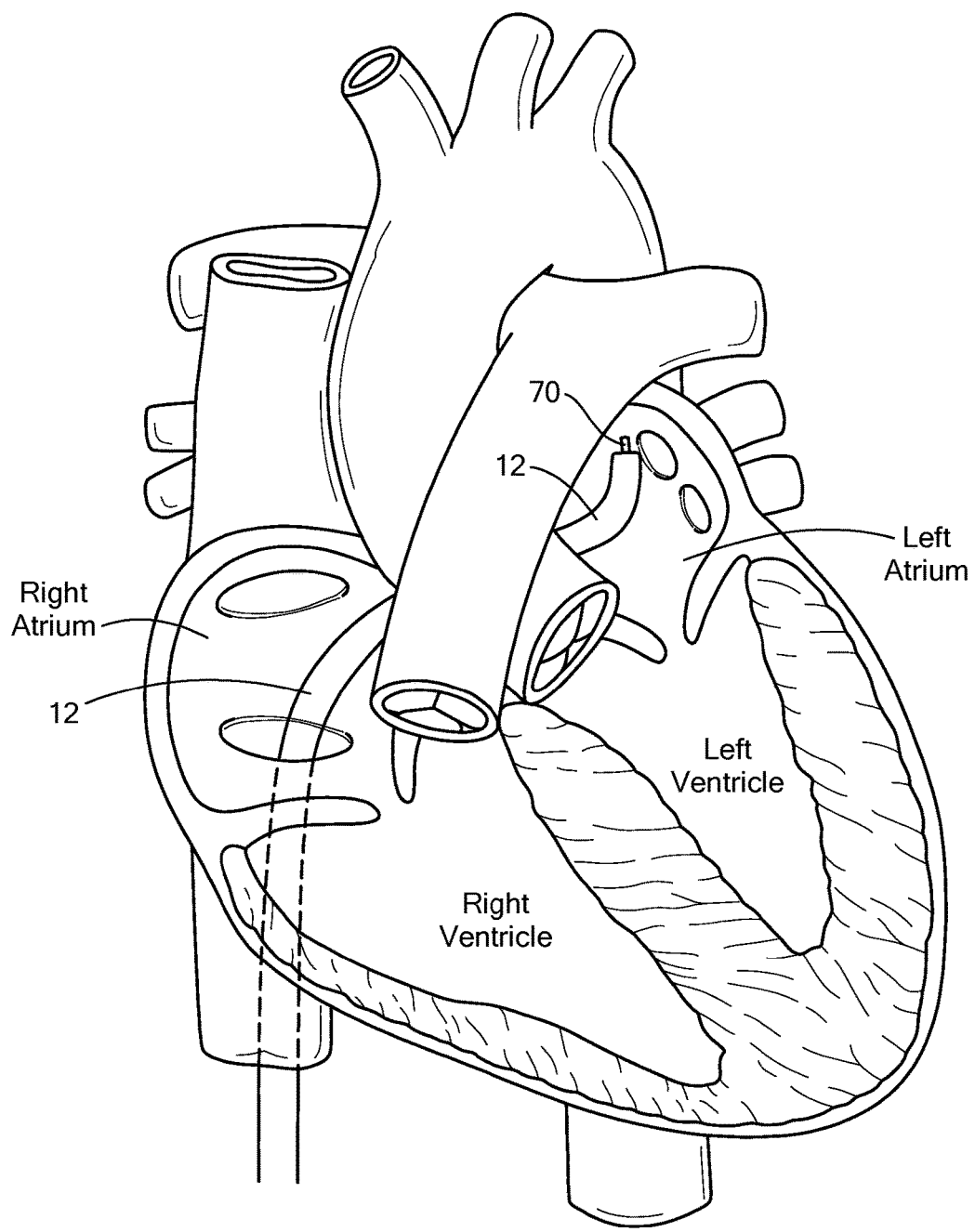
Figure 10:
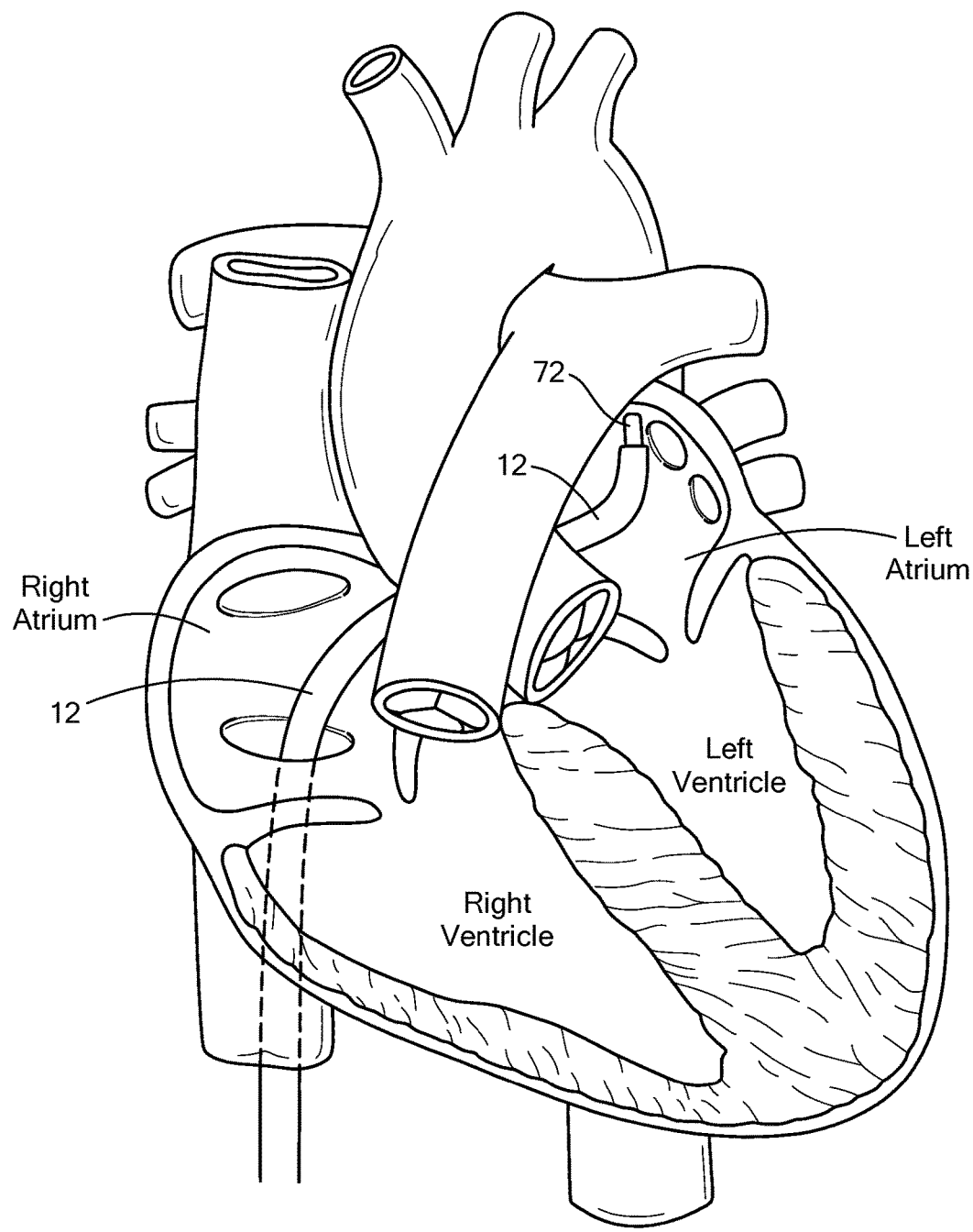

Once the elongate body 16 is at a desired location within the patient's body (for example, within a chamber of the patient's heart), the vacuum pump 36 may be activated and/or put into communication with the space 38 within the jacket 18 so as to generate a negative-pressure environment within the elongate body 16 (as shown in FIG. 9). The vacuum may cause at least some of the atmospheric to exit the space 38, thereby causing the jacket 18 to constrict the plurality of segments 24 within. This increases friction between adjacent segments 24 and between the plurality of segments 24 and the inner surface of the jacket 18. The increased frictional force may substantially increase the rigidity of the elongate body 16, depending in part on the amount of vacuum applied and/or the duration of vacuum application. Thus, the elongate body 16 may be transitioned from a flexible state to a rigid or semi-rigid state without the need for pull wires or other tensioning devices, thereby allowing a treatment device or other secondary medical device to pass through the guidewire lumen. The elongate body 16 and/or other parts of the system 10 between the jacket 18 and the vacuum pump 36 may include one or more valves or vents (not shown) for the automatic or manual regulation of vacuum pressure within the system 10 (for example, for increasing or reducing the amount of vacuum pressure within the jacket 18). The increased frictional force may essentially lock the segments 24 against each other and against the inner surface of the jacket 18, so that the elongate body 18 retains the shape, however curved or tortuous, it took over the guidewire 70, even after the guidewire is removed. For example, FIGS. 3B, 4B, 5B, and 6B show the elongate body 16 in a curvilinear configuration. Once the elongate body 16 is sufficiently rigid so that it is not deformable from an applied external or internal pressure, an over-the-wire secondary medical device 72 (such as a cryoballoon catheter) may be advanced over the guidewire 70 through the guidewire lumen 30 of the elongate body 16 to deliver the secondary medical device to the target treatment site (as shown in FIG. 10). Alternatively, the guidewire 70 may be first removed from the guidewire lumen 30 of the elongate body 16, and then a secondary medical device 72 may be advanced within the guidewire lumen 30 to the target treatment site.

Figure 11A:
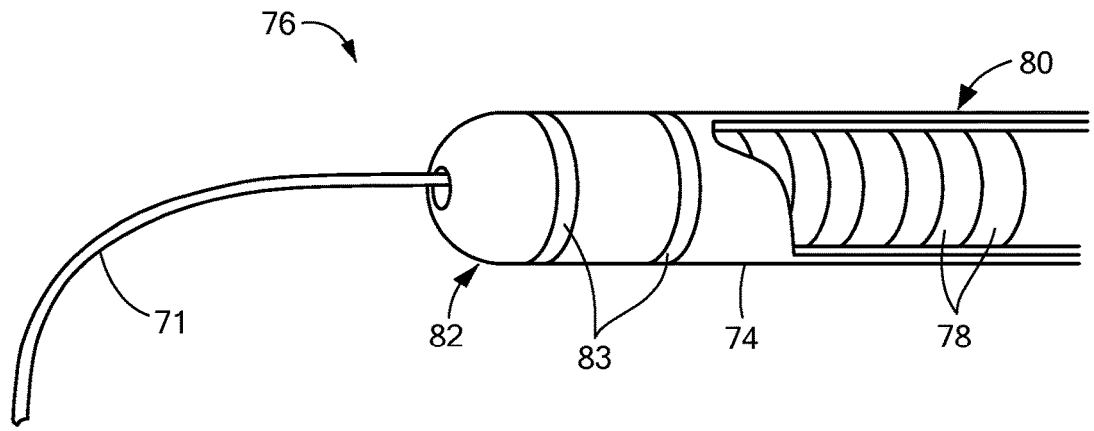
FIG. 11A shows a treatment device having an elongate body with a plurality of segments and electrodes.
Figure 11B:
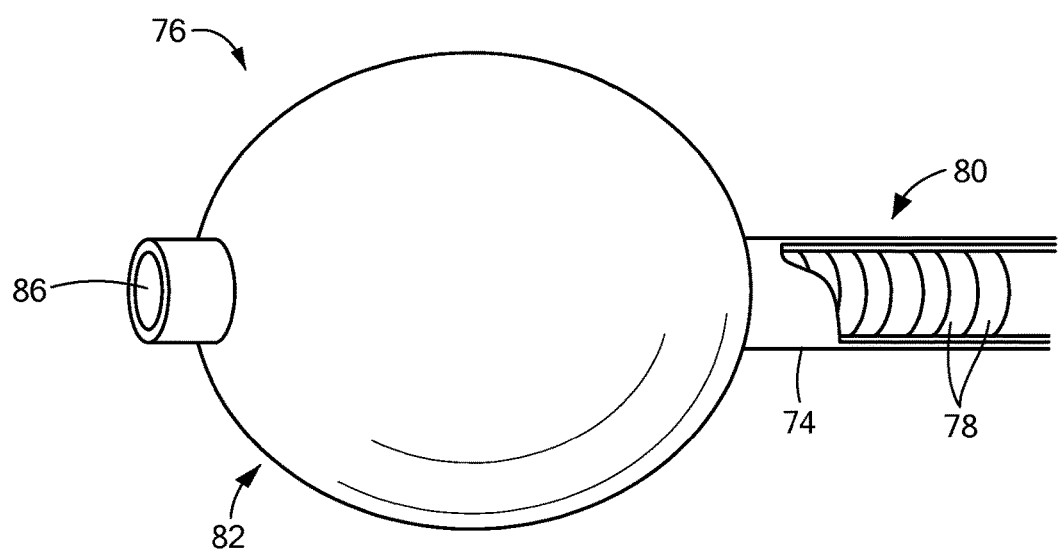
FIG. 11B shows a treatment device having an elongate body with a plurality of segments and a balloon.

Referring now to FIGS. 11A and 11B, treatment devices having an elongate body with a plurality of segments is shown. The elongate body 74 of the treatment device 76 may be generally the same as that shown and described in FIGS. 1-10. That is, the elongate body 74 may include a plurality of segments 78 and/or a segment body (not shown), and a jacket 80. The jacket 80 may be in fluid communication with a vacuum pump so that a vacuum may be applied to the interior of the jacket 80 to constrict the jacket 80 about the segments 78, thus transitioning the elongate body 74 from a flexible state to a rigid or semi-rigid state. The treatment device 76 may further include a distal region 82 including one or more treatment elements, such as the electrodes 83 shown in FIG. 11A or the balloon 84 shown in FIG. 11B. In FIG. 11A, the distal region 82 may have a diameter that is continuous with the elongate body 74 (for example, like a focal catheter) and may include one or more treatment and/or mapping electrodes 83. As shown in FIG. 11B, a balloon 84 may be coupled to the elongate body 74 in the distal region 82. Further, the balloon 84 may be in fluid communication with one or more fluid reservoirs for the delivery and recovery of fluid, such as coolant and/or inflation medium. Although not shown, the fluid delivery and recovery conduits may travel the length of the elongate body 74 along an outer surface of the elongate body. To prevent the fluid conduits from snagging tissue and/or other parts of the system, the conduits may be coupled, for example, adhered, along their length to the elongate body 74 so no gaps exist.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for the delivery of a medical device, the system comprising:
   an elongate body, the elongate body including a plurality of annular segments and a jacket disposed about the plurality of annular segments and defining an interior space, an entirety of the jacket being composed of a single continuous piece of material, at least a portion of each of the plurality of annular segments being located within the interior space of the jacket; and a vacuum source in fluid communication with the interior space of the jacket, the vacuum source being selectively activated and deactivated, the plurality of annular segments being uncoupled from each other when the vacuum source is deactivated.

2. The system of claim 1, wherein the plurality of segments are substantially coaxial with each other when the elongate body is in a linear configuration.

3. The system of claim 2, wherein the plurality of segments are coaxial with each other when the elongate body is in a linear configuration.

4. The system of claim 2, wherein each of the plurality of segments defines a first opening and a second opening.

5. The system of claim 4, wherein the elongate body further includes a central lumen, an outer diameter of the central lumen being defined by at least the first opening of each of the plurality of segments.

6. The system of claim 4, wherein at least a portion of the jacket is in contact with at least the first opening of each of the plurality of segments when the vacuum source is activated.

7. The system of claim 6, wherein at least a portion of the jacket is in contact with at least a portion of an external surface of each of the plurality of segments when the vacuum source is activated.

8. The system of claim 4, wherein the first opening has a smaller diameter than the second opening.

9. The system of claim 4, wherein an inner diameter of first opening is substantially the same as an inner diameter of the second opening.

10. The system of claim 1, wherein activation of the vacuum source causes the elongate body to transition from a flexible state to a rigid state.

11. The system of claim 10, wherein the plurality of segments are movable with respect to each other when the elongate body is in the flexible state, and the plurality of segments are immovable with respect to each other when the elongate body is in the rigid state.

12. The system of claim 11, wherein each of the plurality of segments is annular.

13. The system of claim 11, wherein each of the plurality of segments is concave and substantially hemispherical and defines a first opening and a second opening.

14. The system of claim 13, wherein one or more of the plurality of segments is each disposed within the concavity of an adjacent segment.

15. The system of claim 11, wherein each of the plurality of segments is hollow and conical and defines a first opening and a second opening.

16. The system of claim 15, wherein one or more of the plurality of segments is each disposed within the hollow portion of an adjacent segment.

17. A system for the delivery of a medical device, the system comprising:
   an elongate body, the elongate body including:
      a plurality of discrete annular segments, each of the plurality of annular segments including an inner surface and an outer surface,
      a jacket disposed about the plurality of annular segments, the jacket including an inner portion, an outer portion, and an interior space between the inner and outer portions, the inner portion of the jacket and the outer portion of the jacket being composed of a single piece of material, the plurality of annular segments being located within the interior space of the jacket; and
      a central lumen, a diameter of the central lumen being defined by at least a portion of each of the plurality of annular segments and an inner surface of the central lumen being defined by the inner portion of the jacket; and
   a vacuum source in fluid communication with the interior space of the jacket, activation of the vacuum removing atmospheric air from the interior space of the jacket and increasing frictional forces between the plurality of annular segments and the inner surface of the jacket, the plurality of segments being uncoupled to each other and movable with respect to each other and the interior space of the jacket having a first volume when the vacuum source is inactive, and the plurality of segments are immovable with respect to each other and the interior space of the jacket having a second volume that is less than the first volume when the vacuum source is activated.

18. A method for transitioning an elongate body between a flexible state and a rigid state, the method comprising:
   providing an elongate body, the elongate body including:
      a plurality of discrete annular elements;
      a jacket defining an inner surface, an outer surface, and an interior space between the inner surface and the outer surface, the jacket being composed of a single continuous piece of material, the plurality of elements being located within the interior space and the interior space being in fluid communication with a vacuum source; and
   activating the vacuum source to remove at least a portion of atmospheric air from within the interior space.

* * * * *